United States Patent [19]

Kanegae et al.

[11] Patent Number: 4,728,610
[45] Date of Patent: Mar. 1, 1988

[54] METHOD FOR PRODUCING L-GLUTAMIC ACID

[75] Inventors: Yukihiro Kanegae; Yoshio Sugiyama; Isamu Nakatsui, all of Takasago, Japan

[73] Assignee: Takeda Chemical Industries, Ltd., Osaka, Japan

[21] Appl. No.: 924,141

[22] Filed: Oct. 27, 1986

Related U.S. Application Data

[63] Continuation of Ser. No. 580,636, Feb. 16, 1984, abandoned.

[30] Foreign Application Priority Data

Mar. 18, 1983 [JP] Japan ................................ 58-46712

[51] Int. Cl.[4] .................. C12P 13/24; C12P 13/14; C12R 1/13; C12R 1/15
[52] U.S. Cl. .................... 435/107; 435/110; 435/111; 435/840; 435/843; 435/253
[58] Field of Search ............... 435/240, 241, 253, 110, 435/111, 840, 843

[56] References Cited

U.S. PATENT DOCUMENTS 4,368,266  1/1983  Tosaka et al. ................. 435/110

FOREIGN PATENT DOCUMENTS 0114393  9/1980  Japan .
1224893  3/1971  United Kingdom .

Primary Examiner—Thomas G. Wiseman
Assistant Examiner—Stephanie Seidman
Attorney, Agent, or Firm—Wenderoth, Lind & Ponack

[57] ABSTRACT

L-Glutamic acid is produced in a high yield by cultivating an L-glutamic acid-producing microorganism which requires oleic acid but does not require biotin for growth in a culture medium containing an oleic acid compound and a biotin compound of no less than 100 μg/liter as biotin, with carbohydrate and acetic acid as carbon sources being maintained in a weight ratio of about 80:20 through about 40:60.

7 Claims, No Drawings

METHOD FOR PRODUCING L-GLUTAMIC ACID

This application is a continuation, of now abandoned application Ser. No. 580,636, filed Feb. 16, 1984.

This invention relates to a method for producing L-glutamic acid.

A variety of processes have heretofore been proposed for the commercial-scale production of L-glutamic acid by fermentation techniques, and a fermentation method employing a microorganism which requires oleic acid but does not require biotin for growth has been proposed as a commercially advantageous process for the production of L-glutamic acid. The present inventors have researched means for developing a still more advantageous process, which would ensure a higher production yield of L-glutamic acid and have found that a remarkably greater conversion of carbon sources to L-glutamic acid can be realized by cultivating an L-glutamic acid-producing microorganism which requires oleic acid but does not require biotin for growth in a medium containing oleic acid and an excess amount of biotin with the ratio of carbohydrate to acetic acid being maintained in a fixed range. The present invention is based on the above findings and further studies.

This invention is directed to a method for producing L-glutamic acid characterized in that an L-glutamic acid-producing microorganism which requires oleic acid but does not require biotin for growth is cultivated in a culture medium containing an oleic acid compound and a biotin compound of no less than 100 μg/liter as biotin, with a carbohydrate and acetic acid as carbon sources being maintained in a weight ratio of about 80:20 through about 40:60.

The microorganism employed in this invention is an L-glutamic acid-producing microorganism which requires oleic acid but does not require biotin for growth (hereinafter referred to sometimes as L-glutamic acid-producing strain of this invention), irrespective of its taxonomic classification.

Of such strains, the present inventors found that microorganisms belonging to the genus Brevibacterium or the genus Corynebacterium are particularly useful for the purposes of this invention. For instance, *Brevibacterium thiogenitalis* D-248, *Brevibacterium flavum* BN-11 and *Corynebacterium glutamicum* No. 534-MS-023 may be mentioned as representative L-glutamic acid-producing strains of this invention.

The strains just mentioned have been deposited with the Institute for Fermentation, Osaka (IFO), Japan and the Fermentation Research Institute, Agency of Industrial Science and Technology, Ministry of International Trade and Industry (FRI), Japan. The deposits of the strains at FRI were converted to deposits under the Budapest Treaty and the strains have been stored at FRI. The deposit numbers and the deposit dates are shown in Table 1.

TABLE 1

| Strains | IFO Deposit Number Deposit Date | FRI Deposit Number Deposit Date | Deposit number under the Budapest Treaty |
| --- | --- | --- | --- |
| *Brevibacterium thiogenitalis* D-248 | IFO 12331 December 25, 1965 | FERM P-6989 March 10, 1983 | FERM BP-433 |
| *Brevibacterium flavum* BN-11 | IFO 12525 April 12, 1967 | FERM P-6991 March 10, 1983 | FERM BP-435 |
| *Corynebacterium glutamicum* No. 534-MS-023 | IFO 12523 April 12, 1967 | FERM P-6990 March 10, 1983 | FERM BP-434 |

Of these strains, *Brevibacterium thiogenitalis* has the same microbiological characteristics as those mentioned in Japanese Patent Application Publication No. Sho 45 (1970)-942 except that the present strain requires oleic acid and does not require biotin for growth. The microbiological characteristics of Brevibacterium flavum are identical with those described in Japanese Patent Application Publication No. Sho 39 (1964)-17348 except that the present strain requires oleic acid and does not require biotin for growth. The microbiological characteristics of *Corynebacterium glutamicum* are identical with those described in Journal of the Agricultural Chemical Society of Japan 39, 328 (1965) except that the present strain requires oleic acid and does not require biotin for growth.

Generally, microorganisms of the genera Brevibacterium and Corynebacterium are liable to change in characteristics and ready to undergo mutation spontaneously as well as under the influence of artificial mutagenic treatments such as irradiation with X-rays, ultraviolet light or other radiation or treatment with various mutagenic reagents. These mutants, only if they are able to produce L-glutamic acid and require oleic acid but do not require biotin for growth, can invariably be utilized for the purposes of this invention.

The oleic acid compound used in accordance with this invention may be either oleic acid as such or a salt or ester thereof or an oleic acid-containing material. As examples of the salt of oleic acid, the sodium salt, potassium salt and magnesium salt may be mentioned. The ester of oleic acid includes, for example, sorbitan monooleate, polyoxyethylene sorbitan monooleate, polyoxyethylene sorbitan monooleate and polyoxyethylene glycol monooleate as well as the corresponding sesquioleates, trioleates, etc. As examples of said oleic acid-containing material, there may be mentioned lard oil, fats and oils, etc.

In the method according to this invention, the oleic acid compound is added to the medium and the amount of the oleic acid compound is not less than about 60 mg/liter and preferably about 60 to 300 mg/liter as oleic acid. While it is sufficient to add this amount of oleic acid to the initial medium, oleic acid may be added in the course of cultivation to establish the above concentration.

The biotin compound used in accordance with this invention may be either biotin as such or a biotin-active substance.

In the method according to this invention, biotin compound is incorporated in the medium in a concentration of not less than about 100 μg/liter and preferably about 200 to 500 μg/liter as biotin. While it is sufficient to add the indicated amount of biotin to the initial medium, it may be added in the course of cultivation to establish the above-mentioned concentration.

In this invention, carbohydrate and acetic acid are used as carbon sources in the medium. The ratio of carbohydrate to acetic acid is maintained in the range of about 80:20 through about 40:60 by weight and preferably in the range of about 70:30 through about 50:50 by weight and more preferably about 60:40 by weight throughout the entire cultivation period inclusive of the initial medium.

As to the procedure for adding a carbohydrate and acetic acid, it is sufficient to ensure that the two components exist in the medium in the above-mentioned ratio. Therefore, both of them may be added simultaneously or one of them may be supplementarily added when it has been consumed so that the above ratio may be maintained. The main objective is to ensure that the two components be available in the above-mentioned range.

The carbohydrate employed in the method of this invention may be any carbohydrate which the L-glutamic acid-producing microorganism of this invention utilizes to elaborate L-glutamic acid. As examples of such carbohydrate, there may be mentioned glucose, fructose, sucrose, crude sugars, molasses, and various saccharified starches (e.g. tapioca, sago palm, and sweet potato starches) and these carbohydrates may be used as a mixture.

In the method of this invention, acetic acid is added at a level of not more than about 2% (W/V) in the initial medium and, preferably, a level of not more than about 1% (W/V). At intermediate stages of cultivation, acetic acid is added in such amount that the residual acetic acid in the medium will not exceed a level of about 1% (W/V). Acetic acid as used in the method of this invention need not necessarily be acetic acid as such but may be a salt thereof (e.g. sodium salt, potassium salt, ammonium salt, etc.) or a mixture thereof.

If necessary, the medium used according to this invention may contain, in addition to the above-mentioned specific carbon sources, oleic acid and biotin, various other medium components which are commonly employed in L-glutamic acid fermentation, such as various organic and inorganic nitrogen compounds, inorganic metal salts, vitamins, etc. A defoaming agent can also be added to the medium. The method of cultivation need not be a special method different from the conventional method, and aerated stirring culture is performed at an incubation temperature of 25° to 37° C. During the incubation, the pH of the medium is maintained within the range of about pH 7 to about pH 8.5 by using ammonia gas, aqueous ammonia, urea, or an alkali such as sodium hydroxide, potassium hydroxide, etc., either alone or in combination.

Recovery of L-glutamic acid from the fermentation broth can be carried out by conventional procedures.

The method of this invention features a high rate of conversion of the carbohydrate to L-glutamic acid and, therefore, can provide L-glutamic acid in a high yield. Accordingly, the separation and isolation of L-glutamic acid is facilitated and the production cost is reduced.

The following reference and working examples are further illustrative of this invention.

REFERENCE EXAMPLE 1

A seed culture medium containing 20 g of glucose, 2 g of urea, 1 g of $KH_2PO_4$, 0.4 g of $MgSO_4 \cdot 7H_2O$, 20 g of corn steep liquor, 1 g of $CaCO_3$, 4 mg of $CuSO_4 \cdot 5H_2O$, 150 mg of $FeSO_4 \cdot 7H_2O$ and 300 mg of sodium oleate per liter was distributed in 20 ml portions into 200 ml-capacity conical flasks. After sterilization, each flask was inoculated with a loopful of a slant culture of *Brevibacterium thiogenitalis* D-248 (IFO-12331, FERM BP-433) and incubated on a rotary shaker at 28° C. and 200 rpm for 18 hours. The resulting culture was used as the seed culture.

Separately, a main culture medium containing 1% of the carbon sources in the ratio shown in Table 2, 1.5 g of $KH_2PO_4$, 0.4 g of $MgSO_4 \cdot 7H_2O$, 2 g of corn steep liquor, 5 mg of $MnSO_4 \cdot 4-6H_2O$, 200 μg of biotin, 200 mg of sodium oleate and 10 mg of phenol red per liter (pH 7.2) was distributed in 50 ml portions into 200 ml-capacity creased conical flasks. After sterilization, 2.5 ml of the above seed culture was transferred to each flask, and incubation was initiated on a rotary shaker at 32° C. and 200 rpm. Starting 8 hours after the start of incubation, the carbon sources corresponding to the initial carbon source ratio were added at the rate of 0.4% (W/V) relative to the initial medium at a frequency of once every 1 hour for a total of 35 times.

The results are shown in Table 2. In the following description, the degree of growth of the microorganism is expressed in the absorbance of a 50-fold dilution of the culture at 590 nm. The determination of L-glutamic acid was carried out by the Warburg's manometric method using glutamic acid decarboxylase.

TABLE 2

| Ratio* of carbon sources | | Growth** | Yield of L-glutamic acid (%) |
|---|---|---|---|
| Glucose | Acetic acid | | |
| 100 | 0 | 0.29 | 51.3 |
| 80 | 20 | 0.29 | 64.0 |
| 70 | 30 | 0.29 | 68.5 |
| 60 | 40 | 0.29 | 70.8 |
| 50 | 50 | 0.29 | 66.0 |
| 40 | 60 | 0.30 | 63.2 |
| 30 | 70 | 0.27 | 61.2 |
| 20 | 80 | 0.26 | 60.0 |
| 0 | 100 | 0.21 | 55.4 |

*By weight
**Absorbance of a 50-fold dilution of the culture at 590 nm.

It will be apparent from Table 2 that compared with the cases in which either glucose or acetic acid was used alone, the combined use of both in a weight ratio of 80:20 to 40:60 and, particularly, 70:30 to 50:50 results in a remarkably increased yield of L-glutamic acid.

REFERENCE EXAMPLE 2

A fermentation medium containing 6 g of glucose, 5.8 g of ammonium acetate (4 g as acetic acid), 1.5 g of $KH_2PO_4$, 0.4 g of $MgSO_4 \cdot 7H_2O$, 2 g of corn steep liquor, 5 mg of $MnSO_4 \cdot 4-6H_2O$, the amount of biotin shown in Table 3, 200 mg of sodium oleate, and 10 mg of phenol red (pH 7.2) per liter was distributed in 50 ml portions into 200 ml-capacity creased conical flasks. After sterilization, 2.5 ml portions of a seed culture prepared in the same manner as Reference Example 1 were transferred to the flasks and incubation was started on a rotary shaker at 32° C. and 200 rpm. Starting 8 hours after initiation of incubation, 0.5 ml of a 24% (W/V) aqueous solution of glucose (0.12 g as glucose) and 0.5 ml of a 16% (W/V) aqueous solution of acetic acid (0.08 g as acetic acid) previously adjusted to pH 5.5 with aqueous ammonia were fed at 1-hour intervals for a total of 35 times. During this period, utilizing the color of phenol red as an indicator, the pH of the medium was adjusted to the range of 7.2 to 8.0 with 30% sodium hydroxide. The results are shown in Table 3.

TABLE 3

| Biotin (μg/liter) | Growth* | Yield of L-glutamic acid (%) |
| --- | --- | --- |
| 1 | 0.33 | 5.1 |
| 10 | 0.30 | 6.3 |
| 50 | 0.29 | 29.0 |
| 100 | 0.29 | 65.3 |
| 200 | 0.29 | 71.5 |
| 500 | 0.29 | 71.4 |

*The absorbance of a 50-fold dilution of the culture at 590 nm

Table 3 shows that whereas the growth of the microorganism was hardly influenced by biotin and rather somewhat better growths here obtained at lower concentrations of biotin, the yield of L-glutamic acid increased as the concentration of biotin was increased. It is therefore clear that in order to produce and accumulate L-glutamic acid in high yield, it is necessary to incorporate at least about 100 μg/liter of biotin in the medium.

EXAMPLE 1

A seed culture medium containing 20 g of glucose, 2 g of urea, 1 g of $KH_2PO_4$, 0.4 g of $MgSO_4\cdot 7H_2O$, 20 g of corn steep liquor, 1 g of $CaCO_3$, 4 mg of $CuSO_4\cdot 5H_2O$, 150 mg of $FeSO_4\cdot 7H_2O$ and 300 mg of sodium oleate per liter was distributed in 20 ml portions into 200 ml-capacity conical flasks. After sterilization, these flasks were inoculated with 3 different strains mentioned in Table 4 and incubated at 28° C. on a rotary shaker at 200 rpm for 18 hours. The culture was used as a seed culture.

Separately, a fermentation medium (pH 7.2) containing 6 g of glucose, 5.8 g of ammonium acetate (4 g as acetic acid), 1.5 g of $KH_2PO_4$, 0.4 g of $MgSO_4\cdot 7H_2O$, 2 g of corn steep liquor, 5 mg of $MnSO_4\cdot 6H_2O$, 200 μg of biotin, 200 mg of sodium oleate and 10 mg of phenol red per liter was distributed in 50 ml portions into 200 ml-capacity creased conical flasks. After sterilization, 2.5 ml portions of the above seed culture were transferred to the flasks, and incubation was started at 32° C. on a rotary shaker at 200 rpm. Starting 8 hours after initiation of incubation, 0.5 ml of a 24% (W/V) solution of glucose (0.12 g as glucose) and 0.5 ml of a 16% (W/V) solution of acetic acid (0.08 g as acetic acid) previously adjusted to pH 5.5 with aqueous ammonia were fed simultaneously at 1-hour intervals for a total of 35 times. During this time, using the color of phenol red as an indicator, the pH of the medium was maintained within the range of 7.2 to 8.0 with a 30% solution of sodium hydroxide. The results are shown in Table 4.

TABLE 4

| Strain | Yield of L-glutamic acid (%) |
| --- | --- |
| *Brevibacterium thiogentalis* D-248 (IFO 12331, FERM BP-433) | 71.5 |
| *Brevibacterium fluvum* BN-11 (IFO 12525, FERM BP-435) | 71.0 |
| *Corynebacterium glutamicum* No. 534-MS-023 (IFO 12523, FERM BP-434) | 70.8 |

EXAMPLE 2

The cultivation procedure of Example 1 was repeated for *Brevibacterium thiogenitalis* D-248 (IFO 12331, FERM BP-433) except that sucrose was used as the carbon source in the fermentation medium. The yield of L-glutamic acid based on the carbon source used was 70.8%.

EXAMPLE 3

A fermentation medium (pH 7.2) containing 12 g of an enzymatic hydrolysate of sweet potato starch (as glucose), 11.6 g of ammonium acetate (8 g as acetic acid), 1.5 g of $KH_2PO_4$, 0.4 g of $MgSO_4\cdot 7H_2O$, 2 g of corn steep liquor, 5 mg of $MnSO_4\cdot 4\cdot 6H_2O$, 200 μg of biotin, 175 mg of sodium oleate, and 10 mg of phenol red per liter was distributed in 50 ml portions into 200 ml-capacity creased conical flasks. After sterilization, 2.5 ml of a seed culture of *Brevibacterium thiogenitalis* (IFO 12331, FERM BP-433) prepared in the same manner as Example 1 was transferred to each flask and incubated. Starting 10 hours after initiation of incubation, 0.5 ml of a saccharification liquor containing 30% (W/V) of glucose (0.15 g as glucose) and 0.5 ml of a 20% (W/V) solution of acetic acid (0.1 g as acetic acid) previously adjusted to pH 5.5 with aqueous ammonia were simultaneously fed at 1-hour intervals for a total of 26 times. During the period, the medium was maintained within an range of pH 7.2 to 8.0 with a 30% aqueous solution of sodium hydroxide. The yield of L-glutamic acid based on the carbon sources used was 69.2%.

EXAMPLE 4

A fermentation medium (pH 7.2) containing 14 g of molasses (total sugar), 8.7 g of ammonium acetate (6 g as acetic acid), 1.5 g of $KH_2PO_4$, 0.4 g of $MgSO_4\cdot 7H_2O$, 1 g of corn steep liquor, 5 mg of $MnSO_4\cdot 4\cdot 6H_2O$, 150 μg of biotin, and 150 mg of sodium oleate per liter was fed in a volume of 4 liters into a 10-liter jar fermenter and, after sterilization, was inoculated with 200 ml of a seed culture of *Brevibacterium thiogenitalis* D-248 (IFO 12331, FERM BP-433) prepared in the same manner as Example 1. The incubation was started at 32° C., 500 rpm and 2 liters/min. aeration. When the initial carbon sources had been nearly completely consumed, 0.105% (W/V) of molasses (on a tatal sugar basis) and 0.045% (W/V) of acetic acid, both based on the initial volume of medium, were fed every time the concentration of dissolved oxygen increased so that the incubation was continued until the total amount of carbon sources used reached 15% (W/V) of the initial liquor volume. During this period, the pH of the medium was automatically maintained within the range of 7.3 to 7.7 with aqueous ammonia. The cultivation was completed in about 30 hours, at the end of which time 62.5 mg/ml of L-glutamic acid had been accumulated in the culture broth (6.1 liters). Thus, the yield based on carbon sources was 63.5%. When the broth was treated in the routine manner, 328 g of crude crystals of L-glutamic acid were obtained.

EXAMPLE 5

A fermentation medium (pH 7.2) containing 12 g of glucose, 11.6 g of ammonium acetate (8 g as acetic acid), 1.5 g of $KH_2PO_4$, 0.4 g of $MgSO_4\cdot 7H_2O$, 2 g of corn steep liquor, 5 mg of $MnSO_4\cdot 4\cdot 6H_2O$, 200 μg of biotin and 200 mg of sodium oleate per liter was fed in a volume of 4 liters into a 10-liter jar fermenter and, after sterilization, was inoculated with 200 ml of a seed culture of *Brevibacterium thiogenitalis* D-248 (IFO 12331, FERM BP-433) prepared as in Example 1. The incubation was started at 32° C., 500 rpm and 2 liters/ml aeration. Then, molasses and acetic acid (previously adjusted to pH 5.5 with aqueous ammonia) were fed in the same proportions as in Example 4 until the total amount of carbon sources used became 16% (W/V). The pH of the medium was, however, adjusted with 30% sodium hydroxide. The cultivation was completed in about 36 hours, at which time 67.1 mg/ml of L-glutamic acid was found in the culture broth (6.2 liters). The yield based on carbohydrates was 65%. When L-glutamic acid was recovered from this broth in the routine manner, 370 g of crude crystals were obtained.

What we claim is:

1. A method for producing L-glutamic acid, which comprises cultivating an L-glutamic acid-producing microorganism which requires oleic acid but does not require biotin for growth in a culture medium containing an oleic acid compound and a biotin compound of no less than 100 μg/liter as biotin, with carbohydrate and acetic acid as carbon sources being maintained in a weight ratio of about 70:30 through about 50:50, said microorganisms being from the group consisting of *Brevibacterium thiogenitalis* D-248, Ferm BP-433, *Brevibacterium flavum* BN-11, Ferm BP-435 and *Corynebacterium glutamicum* No. 534-MS-023, Ferm BP-434.

2. A method as claimed in claim 1, wherein the carbohydrate is glucose.

3. A method as claimed in claim 1, wherein the carbohydrate is sucrose.

4. A method as claimed in claim 1, wherein the carbohydrate is saccharified starch of sweet potato.

5. A method as claimed in claim 1, wherein the carbohydrate is molasses.

6. A method as claimed in claim 1, wherein the carbohydrate and acetic acid are maintained in the culture medium in a weight ratio of about 60:40.

7. A method as claimed in claim 1, wherein the amount of the oleic acid compound contained in the medium is not less than about 60 mg/liter.

* * * * *